(12) United States Patent
Korman

(10) Patent No.: US 9,393,390 B2
(45) Date of Patent: Jul. 19, 2016

(54) METHOD AND SYSTEM FOR PROGRAMMED IN SITU TISSUE EXPANSION

(71) Applicant: Marz Medical, Inc., Mountain View, CA (US)

(72) Inventor: Joshua Korman, Los Altos Hills, CA (US)

(73) Assignee: Marz Medical, Inc., Mountain View, CA (US)

( * ) Notice: Subject to any disclaimer, the term of this patent is extended or adjusted under 35 U.S.C. 154(b) by 0 days.

(21) Appl. No.: 14/468,908

(22) Filed: Aug. 26, 2014

(65) Prior Publication Data

US 2016/0058987 A1     Mar. 3, 2016

(51) Int. Cl.
*A61M 29/02* (2006.01)
*A61M 39/22* (2006.01)
*A61M 39/10* (2006.01)

(52) U.S. Cl.
CPC .............. *A61M 29/02* (2013.01); *A61M 39/10* (2013.01); *A61M 39/22* (2013.01); *A61M 2205/3334* (2013.01); *A61M 2205/3337* (2013.01); *A61M 2205/3379* (2013.01)

(58) Field of Classification Search
CPC ............ A61B 19/24; A61B 17/12022; A61M 25/1018–25/10188
USPC ........................................................ 606/192
See application file for complete search history.

(56) References Cited

U.S. PATENT DOCUMENTS

| | | | |
|---|---|---|---|
| 4,955,905 | A | 9/1990 | Reed |
| 5,005,591 | A | 4/1991 | Austad |
| 5,092,348 | A | 3/1992 | Dubrul |
| 5,496,368 | A | 3/1996 | Wiese |
| 5,549,672 | A | 8/1996 | Maddock et al. |
| 6,432,081 | B1 | 8/2002 | Atala |
| 6,668,836 | B1 | 12/2003 | Greenburg et al. |
| 2004/0147953 | A1 | 7/2004 | Gedebou |
| 2008/0051822 | A1* | 2/2008 | Widgerow ............... 606/192 |
| 2010/0010531 | A1 | 1/2010 | Shalon et al. |
| 2011/0152913 | A1 | 6/2011 | Jones et al. |
| 2013/0079807 | A1* | 3/2013 | Korman ................... 606/192 |

OTHER PUBLICATIONS

Logan, et al. A control unit for maximal-rate continuous tissue expansion (CTE). Biomed Sci Instrum. 1989;25:27-33.

* cited by examiner

*Primary Examiner* — Todd J Scherbel
(74) *Attorney, Agent, or Firm* — Wilson, Sonsini, Goodrich & Rosati

(57) ABSTRACT

A tissue expansion system includes driver assembly having a syringe pump and a controller held in a common enclosure. The driver assembly is connected to both an inflatable bladder and an inflation medium source. Fluid is delivered from the driver assembly to the inflatable bladder through a pressure sensor. The pump is actuated to deliver predetermined incremental volumes of the inflation medium to the inflatable bladder at spaced apart time intervals. Pressure is monitored and the pumping is interrupted if the pressure exceeds a predetermined high threshold value. Pumping is recommenced when the pressure falls below a lower threshold value until the total incremental delivery volume has been reached.

5 Claims, 6 Drawing Sheets

METHOD AND SYSTEM FOR PROGRAMMED IN SITU TISSUE EXPANSION

BACKGROUND OF THE INVENTION

1. Field of the Invention

The present invention relates generally to medical methods and devices. More particularly, the present invention relates to methods and systems for expanding tissue by delivering incremental volumes of an inflation medium to an implanted expandable bladder while monitoring inflation pressure.

Tissue defects in the skin and other tissues occur from a variety of causes including surgery, burns, traumatic injury, and congenital deformities. Such defects are often characterized by tissue "deficits" where there is insufficient or poor quality skin or tissue present to cover or fill the affected body region in a normal or desired profile or pattern.

Tissue deficit may be treated by stimulating skin expansion and/or tissue growth in the region of the defect. For example, "tissue expanders" may be implanted beneath a region of skin or within a volume of tissue which suffer from the deficit. By gradually inflating or otherwise expanding such tissue expander, the growth of skin and/or tissue can be promoted.

Presently, most tissue expanders are in the form of an implantable balloon with a valve that allows a physician to periodically inflate the balloon to increase its volume over successive office visits. As the patient will typically visit the doctor only about once per week, such periodic inflations often require relatively large volumes of inflation medium which can cause not only patient discomfort, but also tissue ischemia, concavities to underlying structures such as bone, and induce encapsulation of the implant causing capsular contracture and stiffening of tissue around the expander.

In order to address such shortcomings, a number of "continuously" expanding devices have been proposed. For example, in U.S. Patent Publication 2010/0010531, a device is described which allows the patient to periodically trigger a gas source within the implanted expander. Allowing the patient to control expansion, however, has its own drawbacks, and the patient will seldom follow an optimum inflation protocol to achieve the desired tissue expansion. Moreover, the use of a gas as the inflation medium is also disadvantageous.

A particular improvement in this field is found in U.S. Patent Publication No. 2013/0079807, commonly assigned with the present application, which describes a tissue expansion system including a pump, a controller, an inflatable bladder, and a pressure sensor. The pump is adapted for substantially continuous operation in response to a pressure within a subcutaneously inflatable bladder during expansion. Delivery is based solely on monitored pressure, which can sometimes result in overly rapid treatment.

For these reasons, it would be desirable to provide improved and alternative tissue expansion devices. In particular, it would be desirable to provide such devices which continuously and automatically deliver an inflation medium to an implanted expander over time in a more optimal and controlled pattern. It would be further desirable if such expanders and their supporting systems were adapted for patient convenience and comfort to further promote their use. It would be further desirable if such expanders were operated based on parameters in addition to pressure and the other parameters described above. At least some of these objectives will be met by the inventions described here and below.

2. Description of the Background Art

U.S. Patent Publication No. 2013/0079807, commonly assigned with the present application, describes a tissue expansion system including a pump, a controller, and inflatable bladder, and a pressure sensor. The pump is adapted for substantially continuous operation in response to a pressure within a subcutaneously the inflatable bladder during expansion. Other relevant patents and publications include U.S. Pat. Nos. 6,668,836; 6,432,081; 5,549,672; 5,496,368; 5,005,591; 5,092,348; 4,955,905; and U.S. Patent Publications 2011/152913; 2010/010531; 2008/051822; and 2004/147953. See also Logan and Hayden (1989) ISA, Paper #89-0207, pp. 27-33.

SUMMARY OF THE INVENTION

In a first aspect of the present invention, a method for expanding tissue comprises locating an expandable bladder underneath a region of skin, subcutaneous tissue, or muscle to be expanded by introducing saline or another incompressible inflation medium. Preselected, incremental volumes of the incompressible inflation medium are delivered into the inflatable bladder at spaced-apart time intervals where delivery of one incremental volume is completed and delivery of a subsequent preselected incremental volume is commenced after a time delay, typically between 10 minutes and 3 hours, usually from 30 minutes to 2 hours, and typically about once an hour. By making the incremental volumes small, typically from 1 cc to 10 cc, and spacing the incremental inflation as just noted, the tissue expansion occurs at a slow, controlled rate and the tissue is allowed to yield or remodel between active expansion steps. As an additional protection against over stressing the tissue being expanded, pressure of the pumped inflation medium is monitored while each preselected incremental volume of inflation medium is being pumped into the bladder. Pumping is stopped if the monitored pressure exceeds an upper threshold level, typically in the range from 40 mmHg to 50 mmHg. Pumping of the incremental volume will also be terminated when the preselected incremental volume has been delivered to the bladder. If the pumping was stopped because the monitored pressure exceeded the upper threshold level, pumping the incremental volume will be recommenced when the monitored pressure falls back below a lower threshold level, typically in the range from 25 mmHg to 35 mmHg, and pumping of that incremental volume will continue until the preselected incremental volume has been reached or the monitored pressure once again exceeds the upper threshold level. The steps above will be repeated if the monitored pressure once again exceeds the upper threshold level before the preselected incremental volume has been delivered, and delivery of a plurality of subsequent incremental volumes will then begin at the preselected time intervals set forth above until a preselected cumulative volume of the inflation medium has been delivered to the expandable bladder. In the exemplary embodiments, the time required for delivery of each incremental volume of inflation medium will typically be only a small fraction of the time interval between successive incremental deliveries. For example, if the time interval between successive deliveries is on the order of one hour, the time necessary to driver one incremental volume will usually be under one minute. Thus, even if the high pressure threshold is exceeded more that once and pumping is interrupted, there will almost always be sufficient time to complete the delivery of each incremental volume during the time period between delivery of successive incremental volumes.

Usually, the successive incremental volumes and the time intervals between successive deliveries will be the same and within the ranges set forth above. Alternatively, either or both of the successive incremental volumes and the time intervals between successive deliveries may vary and be different at different times in the inflation delivery protocol.

In specific embodiments of the methods of the present invention, locating the expandible bladder may comprise placing the expandable bladder beneath skin in a subcutaneous, subfascial or submuscular plane, located beneath a region of skin or tissue to be expanded. For example, this may be in a subpectoral pocket following mastectomy. The expandable bladder will usually be initially inflated with a volume of saline, typically in the range from 50 cc to 100 cc.

In other embodiments, the expandable bladder may be placed beneath skin, fascia or muscle located adjacent to a defect which, for example may be a burn scar. The expandable bladder will usually be initially inflated with a volume of saline, typically in the range from 20 cc to 100 cc. In these cases, the bladder may be removed after the skin has been expanded to create a flap and the flap is used to cover the defect.

In all these cases, the pumping may be performed with a constant speed positive displacement pump so that the predetermined incremental volume is provided by a predetermined incremental run time for the pump, and the preselected cumulative volume of the inflation medium is provided by a preselected cumulative run time of the pump.

In a second aspect of the present invention, a system for expanding tissue comprises an expandable bladder adapted to be located beneath a region of skin to be expanded. A syringe pump is configured to draw inflation medium from a source and to deliver said inflation medium to the expandable bladder. A pressure sensor is adapted to monitor pressure of the inflation medium being delivered by the syringe pump, and a delivery line connects the syringe pump to the inflatable bladder. A first one-way valve in the delivery line allows fluid from the syringe pump to flow to the inflatable bladder but blocks reverse flow from the bladder to the syringe. A refill line connects the syringe pump to the source, and a second one-way valve in the refill line allows fluid flow from the source to the syringe and blocks reverse flow from the syringe to the source. A controller operates the syringe pump to deliver inflation medium to the inflatable bladder and to draw inflation medium from the source, where said controller drives the syringe pump periodically over a plurality of incremental time periods to deliver a plurality of incremental volumes of the incompressible inflation medium. The controller receives pressure data from the pressure sensor, and the controller stops the pump when a monitored pressure exceeds an upper threshold level and restarts the pump when the monitored pressure falls below a lower threshold value. The controller usually operates the syringe pump for a predetermined incremental run time to deliver the incremental volume to the inflatable bladder.

In specific embodiments of the methods of the present inventions, the controller is programmed to deliver inflation medium until the pressure reaches an upper threshold value in the range from 40 mmHg to 50 mmHg, with pumping of the particular incremental volume being recommenced when the monitored pressure falls below the lower threshold level in the range from 25 mmHg to 35 mmHg. The preselected incremental volume of inflation medium is usually in the range from 1 cc to 10 cc, and the preselected time interval is in often the range from 10 minutes to 3 hours, more usually being in the range from 30 minutes to 2 hours, and typically being one hour.

The controller in preferred systems will be programmed or otherwise configured to pump inflation medium into the bladder and to terminate pumping of the incremental volume when said the incremental volume has been delivered to the bladder or when said the monitored pressure exceeds the upper threshold level. If the pumping was stopped because the monitored pressure exceeded the upper threshold level, the controller will recommence pumping of the incremental volume when the monitored pressure falls back below the lower threshold level and will continue pumping until the entire incremental volume has been reached or the monitored pressure once again exceeds the upper threshold level. The controller will repeat the stopping and recommencing if the monitored pressure once again exceeds the upper threshold level before the entire incremental volume has been delivered. After completing the delivery of each successive incremental volume, the controller will initiate delivery of the next successive incremental volume of inflation medium at a preselected time intervals until a preselected cumulative volume of the inflation medium has been delivered to the expandable bladder.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
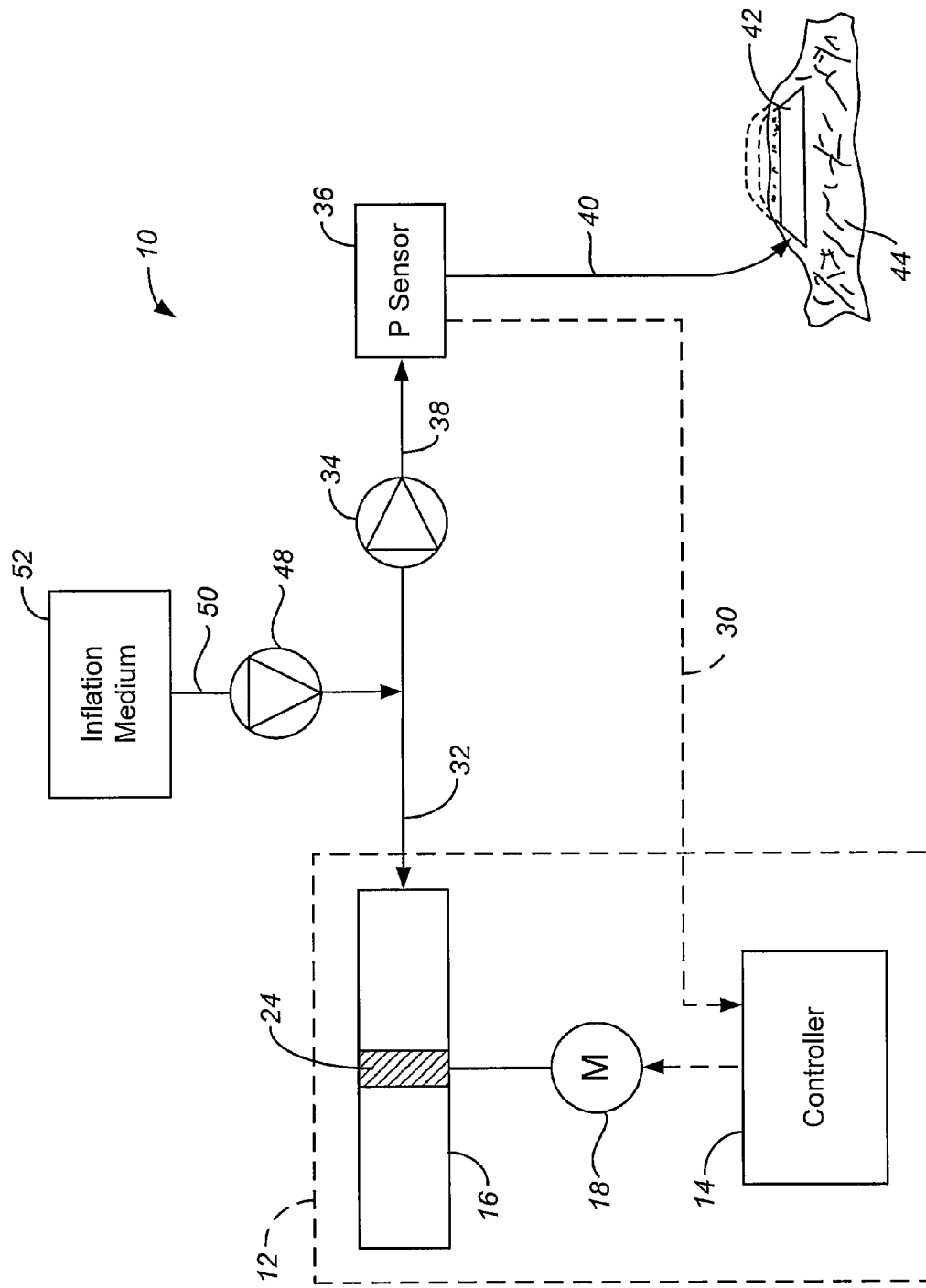
FIG. 1 is a block flow diagram illustrating the system components of an exemplary system constructed in accordance with the principles of the present invention.
Figure 2:
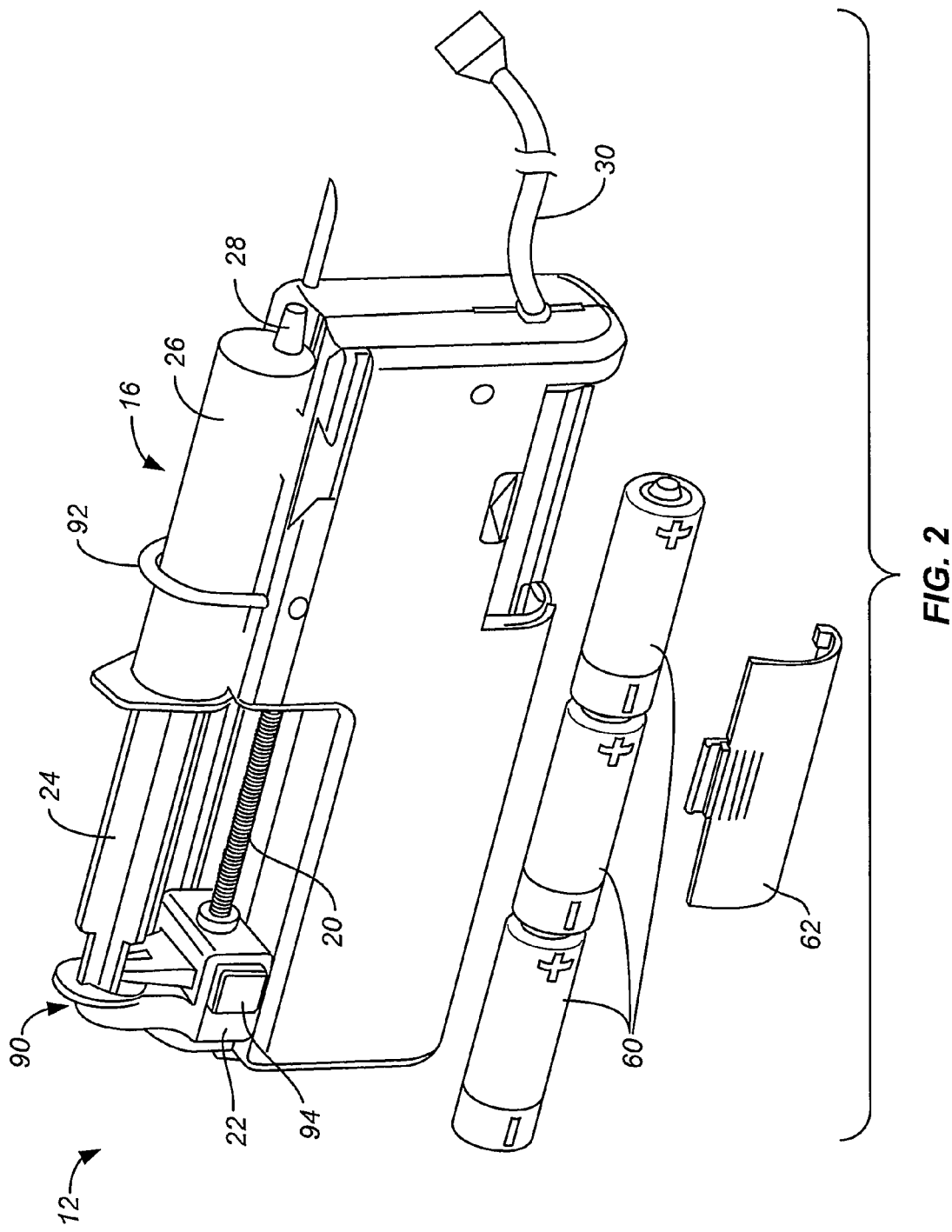
FIG. 2 is a perspective, partially disassembled view of a driver assembly which forms a portion of the exemplary system of FIG. 1.
Figure 3A:
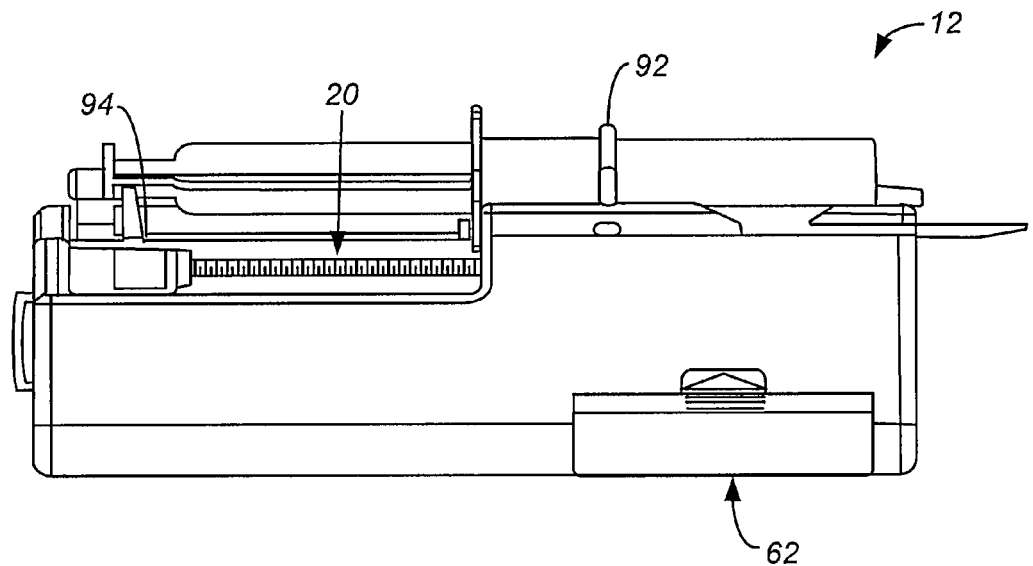
FIGS. 3A and 3B are front and rear views of the driver assembly of FIG. 2.

Referring in particular to FIG. 1, an exemplary system 10 constructed in accordance with the principles of the present invention comprises a driver assembly 12 which includes a controller 14, a syringe 16, and a motor 18. Typically, the motor will drive a lead screw 20 as shown in FIGS. 2 and 3A in order to advance a carriage 22 which is coupled to a plunger 24 of the syringe. The plunger 24, in turn, may either be advanced in a distal direction (to the right in FIG. 2) in order to deliver inflation medium from a barrel 26 of the syringe or may be retracted in a proximal direction in order to draw new inflation medium into the barrel, as will be described in more detail below.

Figure 5:
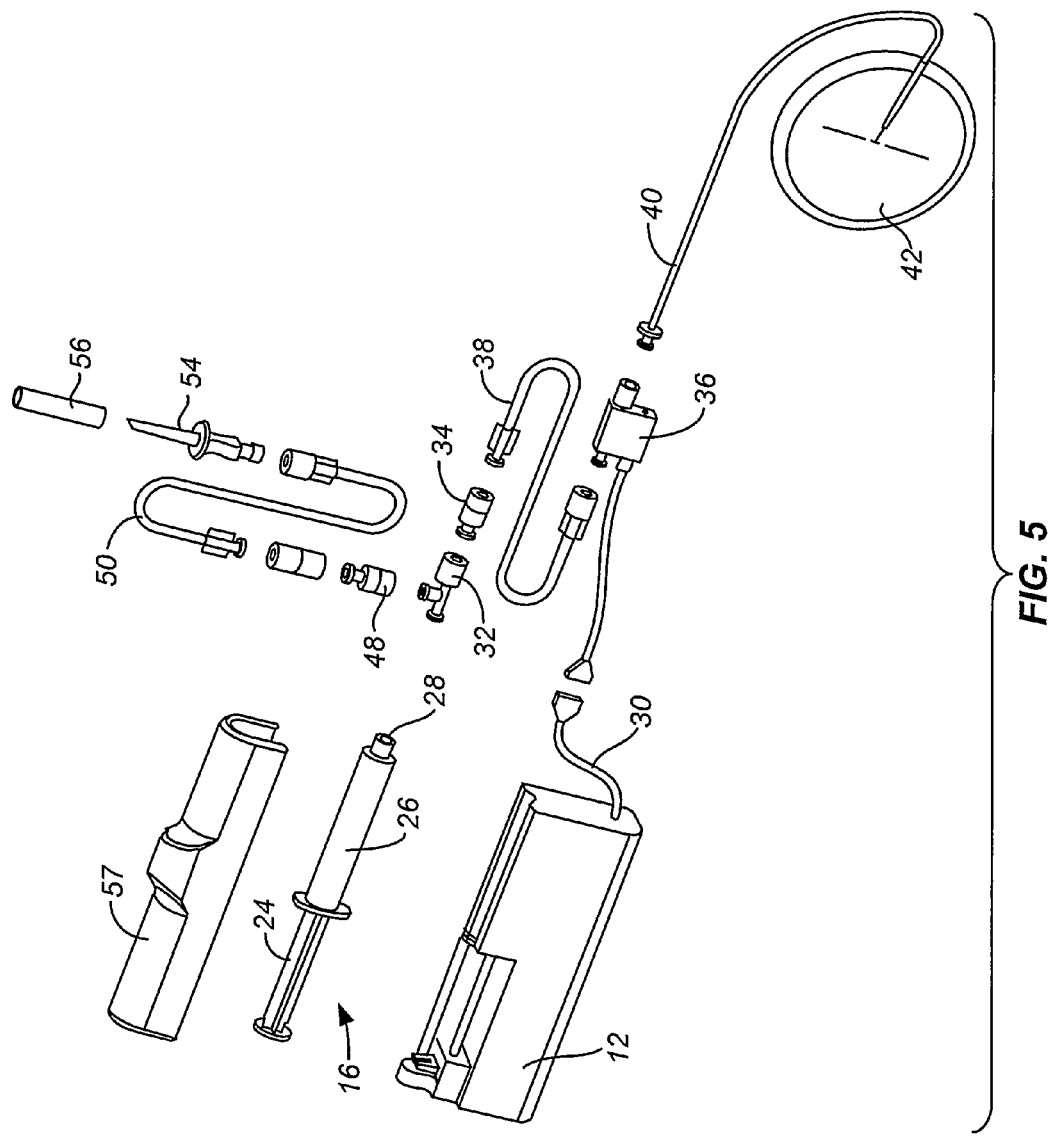
FIG. 5 is an exploded view of the exemplary system of the present invention showing the individual system components.

Referring now to FIGS. 1, 2, and 5, a connector 28 at a distal end of the syringe barrel 26 may be removably connected to a Y-fitting 32 which has two ports which are connected to a first one-way valve 34 and a second one-way valve 48, respectively. The first one-way valve 34, in turn, is removably connected to a connecting tube 38 which connects, at its distal end, to a pressure sensor 36. Pressure sensor 36, in turn, is connected to cable 30 which provides a pressure signal to the controller 14 within the delivery assembly 12. The pressure sensor 36 is further removably connected to a catheter 40 which in turn delivers inflation medium to the expandable and inflatable bladder 42. The first one-way valve 34 is oriented so that it allows flow from the syringe 16, which is caused by advancement of the plunger 24, to pass through the fitting 32, through the fitting 34, to the tube 38, through the pressure sensor 36, and finally through the catheter 40 into the inflatable bladder. The one-way valve 34 will prevent any backflow from the bladder 42 or elsewhere back into the syringe 16, thus reducing the risk of contamination.

The second one-way valve 48, in contrast, is oriented to cause inflation medium from a refill source 52 connected by a connecting tube 50 to flow back into the syringe barrel 26 when the plunger is retracted in order to draw the medium into the syringe. A needle 54 which is connectable to the tubing 15 is configured to be inserted into the source of saline or other inflation medium 52 so that the syringe maybe refilled between successive activations to deliver the inflation medium to the inflatable bladder 42. The controller 14 will be programmed to allow convenient refilling performed by the user. A cover 56 is provided to maintain sterility of the needle between successive uses. Another cover 57 is provided to cover and maintain sterility of the syringe during use.

Figure 3B:
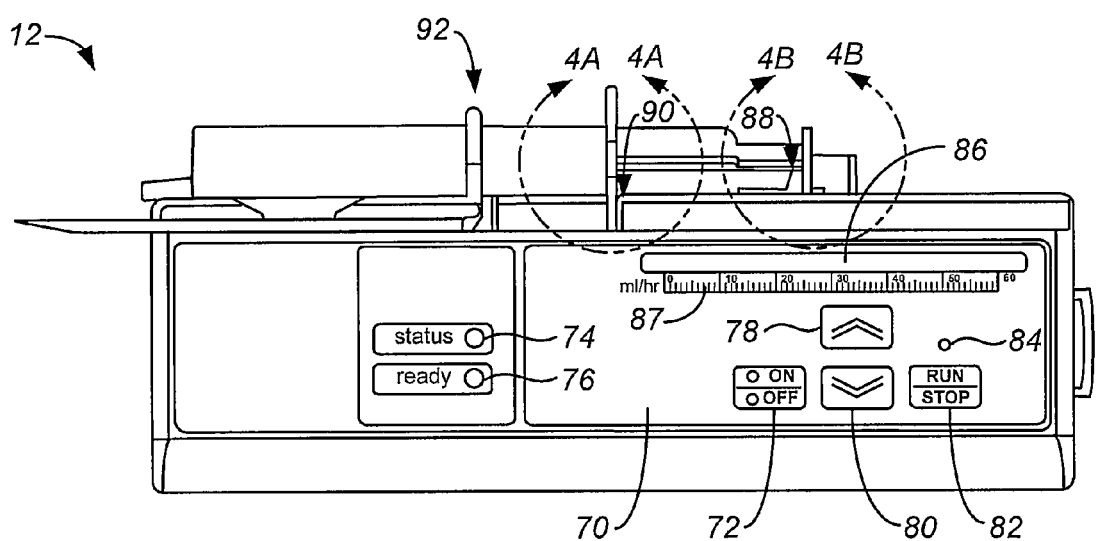

FIGS. 3A and 3B illustrate certain control and other features present on the driver assembly 12 of the systems of the present invention. A battery cover 62 can be removed to replace batteries as shown also in FIG. 2. A touch screen or other display 70 may be provided on the enclosure of the driver as a user interface. The display 70 will include, either virtually or mechanically, a power switch 72, a status light 74, a ready light 76, an incrementing key 78, a decrementing key 80, a run/stop key 82, and a syringe operation indicator 84.

Figure 4A:
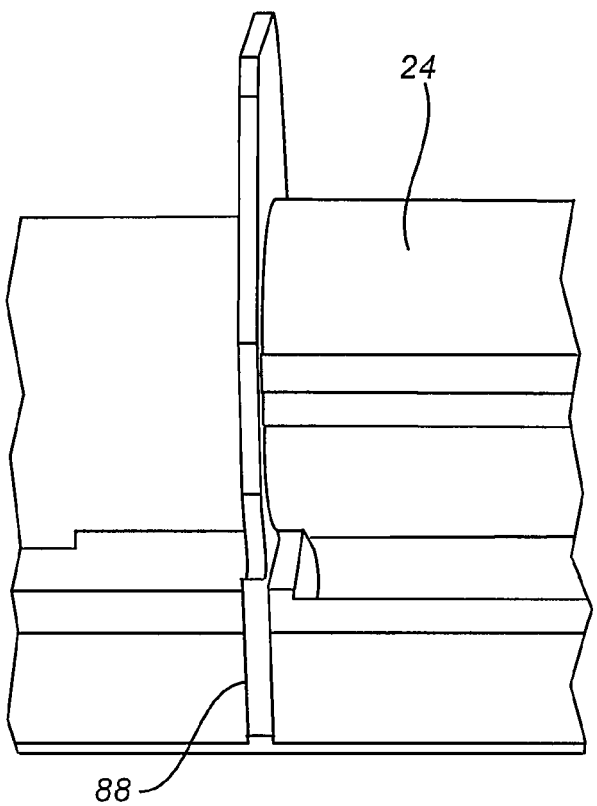
FIGS. 4A and 4B are detailed views taken along the line 4A-4A and line 4B-4B of FIG. 3B.
Figure 4B:
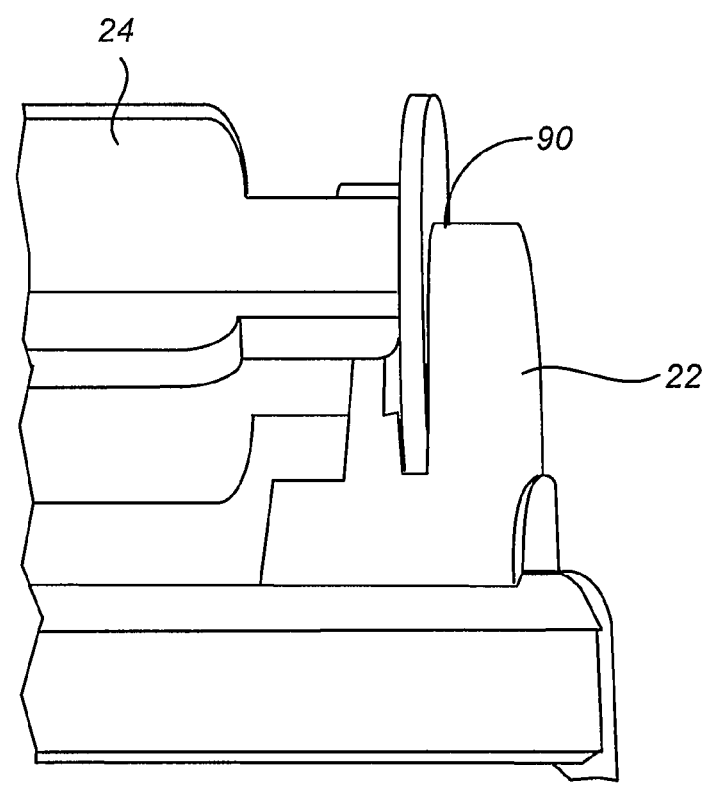

The syringe maybe removed and replaced on the top of the driver assembly 12. In particular, the syringe is held in place by a securing strap 92. The plunger 24 is engaged by a slot 90 in the carriage 22, as best seen in FIG. 4B. Similarly, the syringe barrel flange 88 is held in another slot 88, as best seen in FIG. 4A. The position of the plunger maybe monitored, when the top 57 is in place, with a travel indicator 86 on the display panel 70. The carriage 22 maybe released from the lead screw 20 by a carriage release button 94.

Figure 6:
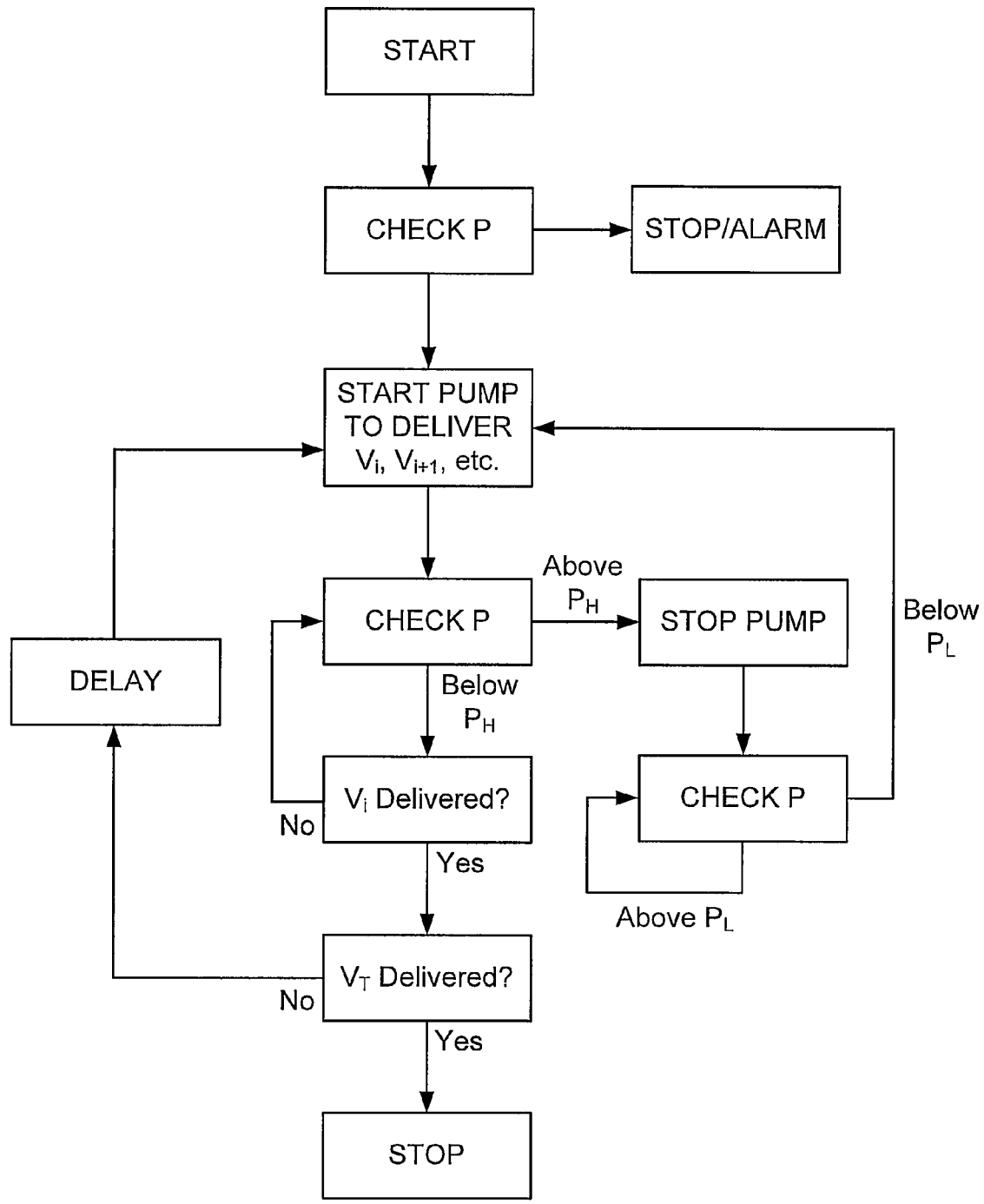
FIG. 6 is a logic diagram illustrating an exemplary operation protocol for the systems of the present invention.

Referring now to FIG. 6, the inflation control system 10 of the present invention may be used by first connecting the catheter 40 to the pressure sensor 36 which in turn has been coupled to the driver 12, as described above. After making sure that the syringe 10 has a sufficient volume of inflation medium, the drive 12 may be turned on using switch 82 which will initiate the sequence of operations illustrated in FIG. 6. Initially, the pressure from sensor 36 is checked. If the pressure exceeds the high pressure threshold level $P_H$, the driver will be stopped and an alert or alarm raised since high pressure should not be present at this point in the protocol. Assuming that the initial pressure check is successful, the controller 14 will initiate power to the motor 18 in order to rotate the lead screw 20 which advances the carriage 22 which in turn drives the plunger 24 at a relatively low rate, typically the volumetric flow ranges set forth about. The pressure sensor 36 will monitor pressure while the syringe is delivering fluid, and the controller 14 will allow continued delivery for so long as the pressure does not exceed the high threshold value $P_H$, again typically within the ranges set forth above. Assuming that no high pressure is detected, the syringe will be driven for a time sufficient to transfer the desired incremental volume $V_i$ to the bladder 42. Typically the volume will be from about 1 cc to 10 cc and it will take from 5 seconds to 60 seconds to complete the delivery.

If, however, the pressure sensor detects a pressure above the high threshold level $P_H$, the controller will stop the pump and continue to monitor the pressure. For so long as the pressure remains above a low pressure threshold $P_L$, which is typically 5 to 10 mmHg lower than the high pressure threshold $P_H$, the pump will remain stopped. As soon as the pressure falls below this lower pressure threshold $P_L$, the pump will be restarted and the inflation medium will continue to be delivered for so long as the pressure remains below the high pressure threshold $P_H$. Pumping will continue until the entire incremental volume $V_i$ has been delivered, at which time the pumping is stopped and not restarted until after the passage of a preselected time interval until the scheduled delivery of the successive incremental volumes $V_{i+1, i+2}, \ldots$, typically in the time ranges set forth above. Such successive incremental volume deliveries will continue until the total cumulative volume $V_T$ of inflation medium has been delivered to the inflatable bladder. Such total volume may take days or even weeks. In some instances, it may be desirable to divide the delivery of the total volume of inflation medium into stages, for example 2, 3, 4, 5, or even more stages, where the time between successive stages is greater than the normal time between the delivery of the incremental volumes.

What is claimed is:

1. A system for expanding tissue, said system comprising:
an expandable bladder adapted to be located beneath a region of skin to be expanded;
a syringe pump configured to draw an incompressible inflation medium into the syringe pump from a source via a common port and to deliver said inflation medium to the expandable bladder via the common port;
a pressure sensor adapted to monitor pressure of the inflation medium being delivered by the syringe pump;
a delivery line connecting the syringe pump to the inflatable bladder;
a first one-way valve in the delivery line that allows fluid flow from the syringe pump to the inflatable bladder and blocks reverse flow from the bladder to the syringe pump;
a refill line connecting the syringe pump to the source;
a second one-way valve in the refill line that allows fluid flow from the source to the syringe pump and blocks reverse flow from the syringe pump to the source; and
a controller which operates the syringe pump to deliver the inflation medium to the inflatable bladder and to draw the inflation medium from the source, wherein said controller drives the syringe pump periodically over a plurality of incremental time periods to deliver a plurality of preselected incremental volumes of the inflation medium while receiving pressure data from the pressure sensor, wherein the plurality of preselected incremental volumes form a preselected cumulative volume, wherein the controller is configured to:
(a) monitor pressure data while each of the incremental volumes of the inflation medium is being pumped into the bladder;
(b) terminate pumping when an individual preselected incremental volume has been delivered to the bladder;
(c) terminate pumping when said monitored pressure exceeds an upper threshold level,
(d) if the pumping was terminated because the monitored pressure exceeded the upper threshold level, recommence pumping when the monitored pressure falls back below a lower threshold level and continue pumping until the individual preselected incremental volume has been delivered;

(e) if the pumping was terminated because the monitored pressure exceeded the upper threshold level, recommence pumping when the monitored pressure falls back below the lower threshold and continue pumping until the monitored pressure once again exceeds the upper threshold level;

(f) repeat step (d) if the monitored pressure once again exceeds the upper threshold level before the individual preselected incremental volume has been delivered; and (g) repeat steps (a) through (f) after a time period until the preselected cumulative volume of the inflation medium has been delivered to the expandable bladder.

2. A system as in claim 1, wherein the controller is programmed to deliver the inflation medium until the pressure reaches the upper threshold value.

3. A system as in claim 1, wherein each of the incremental volumes of the inflation medium is in the range from 1 cc to 10 cc and each of the time intervals is in the range from 10 minutes to 3 hours.

4. A system as in claim 1, wherein the upper threshold level is in the range from 40 mmHg to 50 mmHg and the lower threshold level is in the range from 25 mmHg to 35 mmHg.

5. A system as in claim 1, wherein the controller operates the syringe pump for a predetermined incremental run time to deliver the individual preselected incremental volume to the inflatable bladder.

* * * * *